(12) United States Patent
Beck et al.

(10) Patent No.: US 6,551,604 B1
(45) Date of Patent: Apr. 22, 2003

(54) SKIN CARE COMPOSITIONS

(75) Inventors: Petra Helga Beck, Camberley (GB); Robert Francis Date, Woking (GB); Mario Elmen Tremblay, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/807,151

(22) PCT Filed: Jun. 28, 1999

(86) PCT No.: PCT/US99/14569

§ 371 (c)(1),
(2), (4) Date: Nov. 8, 2001

(87) PCT Pub. No.: WO00/24372

PCT Pub. Date: May 4, 2000

(51) Int. Cl.⁷ .............................. A61K 6/00; A61K 7/00; A61K 31/435
(52) U.S. Cl. ...................... 424/401; 514/277; 514/937; 514/938; 514/947
(58) Field of Search .................................. 514/937, 938, 514/947, 277; 424/401

(56) References Cited

U.S. PATENT DOCUMENTS

| 4,892,726 A | 1/1990 | Yonekura et al. |
| 5,223,559 A | 6/1993 | Arraudeau et al. |
| 5,660,839 A | 8/1997 | Allec et al. |
| 5,939,083 A | 8/1999 | Allec et al. |

FOREIGN PATENT DOCUMENTS

| EP | 0 692 242 B1 | 1/1996 |
| JP | 09-020609 A | 1/1997 |
| WO | WO 98/52533 A | 11/1998 |

*Primary Examiner*—Theodore J. Criares
*Assistant Examiner*—Jennifer Kim
(74) *Attorney, Agent, or Firm*—Kenya T. Pierre; Dara M. Kendall; Tara M. Rosnell

(57) ABSTRACT

The present invention relates to topical compositions for effecting an immediate improvement in the appearance and feel of skin, in addition to providing chronic improvements in skin appearance. The compositions comprise from 0.5% to 25% of a first particulate material having a refractive index of from 1.3 to 1.7, the particulate material being dispersed in the composition and having a median particle size of from 2 to 30 um, and an active effective for chronically regulating skin condition selected from Vitamin B3 compounds, retinoids, and mixtures thereof. Preferred emobodiments are oil in water emulsions further comprising a second particulate material having a larger particle size than the first.

13 Claims, No Drawings

SKIN CARE COMPOSITIONS

This application is a 371 of PCT/US 99/14569, filed Jun. 28, 1999.

TECHNICAL FIELD

The present invention relates to the field of topical compositions for improving the appearance or other condition of skin. More particularly, the invention relates to topical compositions which provide good coverage of skin imperfections, e.g., pores and uneven skin tone, while retaining a natural skin appearance. The compositions of the invention are especially useful for the treatment of hands and other non-facial parts of the body.

BACKGROUND

A variety of compounds have been described in the art as being useful for regulating fine lines, wrinkles and other forms of undesirable skin surface texture. In addition, Vitamin $B_3$ compounds, particularly niacinamide, have recently been found to provide measurable benefits in regulating skin condition, including regulating fine lines, wrinkles and other forms of uneven or rough surface texture associated with aged or photodamaged skin. However, many materials require multiple applications over an extended period to provide such appearance benefits. It would be additionally advantageous to provide a topical composition which provides a more immediate improvement in the appearance of fine lines, wrinkles, pores and other forms of undesirable skin surface texture, and also to effect an immediate improvement in the feel of the skin.

Particulate materials, including both organic and inorganic particles, have been included in skin care compositions. See, for example, 'Quantification of the Soft-Focus Effect', Cosmetics & Toiletries, Vol. 111, July 1996, pp. 57–61, which discloses that one can physically fill in skin lines with a reflective substance such as $TiO_2$. U.S. Pat. No. 4,892,726, issued to Toshiba Silicone Co. Ltd. describes the use of polymethylsilsesquioxane powders in makeup and cosmetic compositions which are smooth upon application and impart natural colour. These particles are now available, in a variety of particle size grades, from Toshiba Silicone Co. Ltd under the name Tospearl®. U.S. Pat. No. 5,223,559 describes the use of a variety of particulate fillers of particle size from 0.5 to 50 μm, particularly from 1 to 15 μm, for blurring skin defects. The particles disclosed therein include Tospearl® 3120 which has a particle size of about 12 μm. Furthermore, EP-A-692,242 disclose the use of hollow, deformable particles of a size of from 1 to 250 μm, most preferably 18 μm for reducing the sticky feel of compositions rich in fatty substances. The compositions of EP-A-692,242 can comprise a wide range of biologically active agents, including retinol and its esters.

Whilst the compositions and disclosures of the prior art provide useful advances in the art of cosmetic skin treatment, they do not adequately teach how to provide both acute and chronic improvements in skin feel and appearance, especially for environmentally stressed areas of the body such as hands.

It has now been found that improvements in both the short and long-term appearance and feel of skin can be enhanced by compositions comprising an active for chronically regulating skin condition, e.g., for regulating fine lines, wrinkles, pores and other forms of undesirable skin surface texture, in addition to one or more particulate actives of defined refractive index and particle size.

It is an object of the present invention to provide topical compositions suitable for imparting an essentially immediate improvement in skin feel and appearance. It is another object of the present invention to provide topical compositions containing a particulate material, e.g. polymethylsilsesquioxane, which provides desirable coverage of skin imperfections such as pores and uneven skin tone, while maintaining a natural skin appearance (e.g. without unacceptable skin whitening). Another object of the present invention is to provide such topical compositions which are additionally useful for chronically regulating skin appearance and/or condition, especially regulating textural or tonal discontinuities in skin (e.g., pores, fine lines, wrinkles, uneven skin colour). It is a particular object of the invention to provide such compositions wherein the composition contains an active for chronically regulating skin condition, in addition to the particulate material.

The present invention also relates to cosmetic methods of improving skin appearance and/or condition by topical application of the subject compositions.

These and other objects of this invention will become apparent in light of the following disclosure.

SUMMARY OF THE INVENTION

The present invention relates to topical compositions comprising:

a) from about 0.5% to about 25% of a first particulate material having a refractive index of from about 1.3 to about 1.7, the particulate material being dispersed in the composition and having a median particle size of from about 2 to about 30 μm;

b) a safe and effective amount of an active effective for chronically regulating skin condition selected from the group consisting of Vitamin B3 compounds, retinoids, and mixtures thereof; and c) a topical carrier.

The compositions are useful for imparting an essentially immediate visual improvement in skin appearance, along with additional visual improvements in skin appearance following multiple topical application of the compositions, while maintaining a natural skin appearance.

The invention further relates to cosmetic methods of improving skin appearance and/or condition by topical application of the subject compositions.

DETAILED DESCRIPTION OF THE INVENTION

All percentages and ratios used herein are by weight of the total composition and all measurements made are at 25° C., unless otherwise designated.

All publications cited herein are hereby incorporated by reference in their entirety.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgement.

Active and other ingredients useful herein may be categorised or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The compositions of the invention are useful for topical application and for providing an essentially immediate (i.e., acute) improvement in skin feel and appearance following application of the composition to the skin. Without intending to be limited by theory, it is believed that this acute improvement results at least in part from therapeutic coverage or masking of skin imperfections by the particulate material. The compositions of the invention are also useful for providing visual improvements in skin appearance or condition following multiple topical applications of the composition to the skin. The compositions provide the visual benefits without imparting an unacceptable skin appearance such as skin whitening.

More particularly, the compositions of the present invention are useful for regulating skin condition, including regulating visible and/or tactile discontinuities in skin, including but not limited to visible and/or tactile discontinuities in skin texture and/or colour, more especially discontinuities associated with skin ageing. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological ageing and other biochemical changes from within the skin.

Regulating skin condition includes prophylactically and/or therapeutically regulating skin condition. As used herein, prophylactically regulating skin condition includes delaying, minimising and/or preventing visible and/or tactile discontinuities in skin. As used herein, therapeutically regulating skin condition includes ameliorating, e.g., diminishing, minimising and/or effacing, such discontinuities. Regulating skin condition involves improving skin appearance and/or feel, e.g., providing a smoother, more even appearance and/or feel. As used herein, regulating skin condition includes regulating signs of ageing. "Regulating signs of skin ageing" includes prophylactically regulating and/or therapeutically regulating one or more of such signs (similarly, regulating a given sign of skin ageing, e.g., lines, wrinkles or pores, includes prophylactically regulating and/or therapeutically regulating that sign).

It is to be understood that the present invention is not to be limited to regulation of the above mentioned "signs of skin ageing" which arise due to mechanisms associated with skin ageing, but is intended to include regulation of said signs irrespective of the mechanism of origin. As used herein, "regulating skin condition" is intended to include regulation of such signs irrespective of the mechanism of origin.

Compositions of the present invention are especially useful for treatment of the hands and other non-facial areas of the body.

Particulate Material

The compositions of the present invention comprise a first particulate material having a refractive index of from about 1.3 to about 1.7, the particulate material being dispersed in the composition and having a median particle size of from about 2 to about 30 $\mu$m. The median particle size is measured when the particulate material is in the neat form i.e. in the essentially pure, powder form prior to combination with the carrier of the invention. Particular methods of measuring particle size may, however, require the particulate material to be dispersed in an inert carrier, such as a pure oil, in order to measure the particle size distribution.

Refractive index can be determined by conventional methods. For example, a method for determining the refractive index which is applicable to the present invention is described in J. A. Dean, Ed., Lange's Handbook of Chemistry, 14th Ed., McGraw Hill, New York, 1992, Section 9, Refractometry, incorporated herein by reference in its entirety. The refractive index is preferably in the range from about 1.35 to about 1.6, this range closely matching the refractive index of skin.

Preferred particulate materials are those having a neat primary particle size of from about 2 to about 15 $\mu$m, more preferably from about 2 to about 10 $\mu$m, even more preferably from about 3 to about 7.5 $\mu$m. Median particle size can be determined by any suitable method known in the art, such as by using coulter-counter equipment or the ASTM Designation E20-85 "Standard Practice for Particle Size Analysis of Particulate Substances in the Range of 0.2 to 75 Micrometers by Optical Microscopy", ASTM Volume 14.02, 1993, incorporated herein by reference.

The compositions of the present invention preferably comprise from about 0.5% to about 25%, more preferably from about 1% to about 20%, especially from about 2% to about 12%, of the first particulate material.

In preferred embodiments, compositions herein comprise a second particulate material having a refractive index of from about 1.3 to about 1.7, preferably in the range from about 1.35 to about 1.6, and having a median particle size of from about 8 to about 30 $\mu$m, preferably from about 10 to about 20 $\mu$m and wherein further the ratio of the median particle size of the first particulate to that of the second particulate is less than about 0.75, preferably less than about 0.6, more preferably less than about 0.5. The refractive index of particular embodiments of the second particulate, when used, can however be the same as or different to particular embodiments of the first particulate material. When used, suitable levels of the second particulate material are from about 0.1% to about 5%, more preferably from about 1% to about 3%. Preferably both the first and second particulates have relatively narrow distributions, by which is meant that more than 50% of the particles fall within 3 $\mu$m either side of the respective median value. Also preferred is that more than 50%, preferably more than 60%, more preferably more than 70% of particles fall within the size ranges prescribed for the respective median values. Without wishing to be bound by theory it is believed that better packing is achieved by the use of two distinct distributions and that this accounts for an improved skin feel and/or appearance when the second particulate is used.

The first and second particulate materials can be inorganic or organic, preferably they are organic or organosilicone, more preferably organosilicone polymers. Preferred particles are free-flowing, solid, materials. By "solid" is meant that the particles are not hollow. The void at the centre of hollow particles can have an adverse effect on refractive index and therefore the visual effects of the particles on either skin or the composition. Suitable organic particulate materials include those made of polymethylsilsesquioxane, referenced above, polyamide, polythene, polyacrylonitrile, polyacrylic acid, polymethacrylic acid, polystyrene, polytetrafluoroethylene (PTFE) and poly(vinylidene chloride). Copolymers derived from monomers of the aforementioned materials can also be used. Inorganic materials include silica and boron nitride.

A representative commercially available example of the first particulate material is Tospearl® 145 which has a median particle size of about 4.5 μm. A further representative commercially available example is Orgasol® 2002 D NAT COS available from Elf Atochem SA, Paris, France, which is an example of a polyamide organic particulate material. A representative commercially available example of the second particulate material is EA-209® from Kobo which is an ethylene/acrylic acid copolymer having a median particle size of about 10 μm.

The compositions may contain other inorganic or organic particulate materials. However, it is preferred that the particulates in the compositions of the invention consist essentially of the particulate material described in this section entitled "Particulate Material."

Active for Chronically Regulating Skin Condition

The compositions of the invention comprise a safe and effective amount of an active for chronically regulating skin condition selected from Vitamin $B_3$ compounds, retinoids, and combinations thereof. The aforementioned compounds may, when used by themselves, give rise to a sticky feel, especially when used at the higher levels. It has been found, however, that this sticky feel can be offset by using the particulates of the present invention. The compositions of the present invention preferably comprise from about 0.1% to about 15%, more preferably from about 0.3% to about 10%, even more preferably from about 1 to about 5% of the active.

Specific examples of these actives include the following.

A. Vitamin $B_3$ Compounds

As used herein, "vitamin $B_3$ compound" means a compound having the formula:

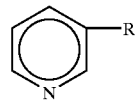

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. As used herein, "non-vasodilating" means that the ester does riot commonly yield a visible flushing response after application to the skin in the subject compositions (the majority of the general population would not experience a visible flushing response, although such compounds may cause vasodilation not visible to the naked eye, i.e., the ester is non-rubefacient). Non-vasodilating esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid ($C_8H_8N_2O_3$) and nicotinyl hydroxamic acid ($C_6H_6N_2O_2$). Exemplary nicotinyl alcohol esters include nicotinyl alcohol esters of the carboxylic acids salicylic acid, acetic acid, glycolic acid, and palmitic acid and the like. Other examples of vitamin $B_3$ compounds useful herein are 2-chloronicotinamide, 6-methylnicotinamide, N-methylnicotinamide, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

Salts of the vitamin $B_3$ compound are also useful herein. Useful examples include organic or inorganic salts, such as inorganic salts with anionic inorganic species (e.g. chloride), and organic carboxylic acid salts. These and other salts of the vitamin $B_3$ compound can be readily prepared by the skilled artisan, for example, as described by W. Wenner, "The Reaction of L-Ascorbic and D-Isoascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

In a preferred embodiment, the ring nitrogen of the vitamin $B_3$ compound is uncomplexed, or after delivery to the skin becomes uncomplexed. More preferably, the vitamin $B_3$ compound is essentially uncomplexed. Therefore, if the composition contains the vitamin $B_3$ compound in a salt or otherwise complexed form, such complex is preferably substantially reversible upon delivery of the composition to the skin. Such complex should be substantially reversible at a pH of from about 5.0 to about 6.0. Such reversibility can be readily determined by one having ordinary skill in the art.

In a preferred embodiment, the vitamin $B_3$ compound typically contains less than about 50% of the compound in a salt form.

The vitamin $B_3$ compound may be included as the substantially pure material, or as an extract obtained by suitable physical and/or chemical isolation from natural (e.g., plant) sources. The vitamin B3 compound is preferably substantially pure, by which is meant substantially free of impurities arising from the original source. Substantially pure compounds can be provided in solution, optionally with an anti-oxidant or other stabiliser.

B. Retinoids

As used herein, "retinoid" includes all natural and/or synthetic analogues of Vitamin A or retinol-like compounds which possess the biological activity of Vitamin A in the skin as well as the geometric isomers and stereoisomers of these compounds. The retinoid is preferably retinol, retinol esters (e.g., $C_2$–$C_{22}$ alkyl esters of retinol, including retinyl palmitate, retinyl acetate, retinyl propionate), retinal, and/or retinoic acid (including all-trans retinoic acid and/or 13-cis-retinoic acid) or its esters such as tocopheryl retinoate. Preferably retinoids other than retinoic acid are used. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun.

23, 1992 to Purcell et al.; and U.S. Pat. No. Reissue 34,075, issued Sep. 22, 1992 to Purcell et al. Preferred retinoids are the retinol esters such as retinyl palmitate, retinyl acetate, and retinyl propionate. Most preferred are retinyl propionate and retinyl palmitate.

The retinoid may be included as the substantially pure material, or as an extract obtained by suitable physical and/or chemical isolation from natural (e.g., plant) sources. The retinoid is preferably substantially pure.

The compositions of this invention contain a safe and effective amount of the retinoid, such that the resultant composition is safe and effective for regulating skin condition, preferably for regulating visible and/or tactile discontinuities in skin, more preferably for regulating signs of skin ageing, even more preferably for regulating visible and/or tactile discontinuities in skin texture associated with skin ageing. The compositions preferably contain from about 0.005% to about 2%, more preferably 0.01% to about 2%, retinoid. Retinol is most preferably used in an amount of from or about 0.01% to about 0.15%; retinol esters are most preferably used in an amount of from about 0.01% to about 2% (e.g., about 1%); retinoic acids are most preferably used in an amount of from about 0.01% to about 0.25%; tocopheryl retinoate is preferably used in an amount of from about 0.01% to about 2%. The compositions herein can comprise both a retinoid and a Vitamin $B_3$ compound.

Carrier

The compositions of the present invention comprise a safe and effective amount of a dermatologically acceptable carrier, suitable for topical application to the skin within which the essential materials and optional other materials are incorporated to enable the essential materials and optional components to be delivered to the skin at an appropriate concentration. The carrier can thus act as a diluent, dispersant, solvent, or the like for the particulate material(s) and the active which ensures that they can be applied to and distributed evenly over the selected target at an appropriate concentration.

The carrier can be solid, semi-solid or liquid. Highly preferred carriers are liquid or semi-solid, such as creams, lotions and gels. Preferably the carrier is in the form of a lotion, cream or a gel, more preferably one which has a sufficient thickness or yield point to prevent the particles from sedimenting. The carrier can itself be inert or it can possess dermatological benefits of its own. The carrier should also be physically and, chemically compatible with the essential components described herein, and should not unduly impair stability, efficacy or other use benefits associated with the compositions of the present invention.

The type of carrier utilised in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

Preferred carriers contain a dermatologically acceptable, hydrophilic diluent. Suitable hydrophilic diluents include water, organic hydrophilic diluents such as $C_1$–$C_4$ monohydric alcohols and low molecular weight glycols and polyols, including propylene glycol, polyethylene glycol (e.g. of MW 200–600), polypropylene glycol (e.g. of MW 425–2025), glycerol, butylene glycol, 1,2,4-butanetriol, sorbitol esters, 1,2,6-hexanetriol, ethanol, iso-propanol, sorbitol esters, ethoxylated ethers, propoxylated ethers and combinations thereof. The diluent is preferably liquid. Water is an especially preferred diluent. The composition preferably comprises at least about 60% of the hydrophilic diluent.

Preferred carriers comprise an emulsion comprising a hydrophilic phase, especially an aqueous phase, and a hydrophobic phase e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 50% (preferably about 1% to about 30%) of the dispersed hydrophobic phase and from about 1% to about 99% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase. The emulsion may also comprise a gel network, such as described in G. M. Eccleston, Application of Emulsion Stability Theories to Mobile and Semisolid O/W Emulsions, Cosmetics & Toiletries, Vol. 101, November 1996, pp. 73–92, incorporated herein by reference. Preferred compositions herein are oil-in-water emulsions.

Preferred compositions have an apparent viscosity of from about 5,000 to about 200,000 mPa.s (centipoise). For example, preferred lotions have an apparent viscosity of from about 10,000 to about 40,000 mPa.s; preferred creams have an apparent viscosity of from about 30,000 to about 160,000 mPa.s. Apparent viscosity can be determined using a Brookfield DVII RV viscometer, spindle TD, at 5 rpm, or the equivalent thereof. The viscosity is determined on the composition after the composition has been allowed to stabilise following its preparation, generally at least 24 hours under conditions of 25° C.+/−1° C. and ambient pressure after preparation of the composition. Apparent viscosity is measured with the composition at a temperature of 25° C.+/−1° C., after 30 seconds spindle rotation.

The compositions of the present invention are usually formulated to have a pH of 9.5 or below and in general have a pH in the range from about 4.5 to about 9, more preferably from about 5 to about 8.5.

Some compositions, particularly those comprising an additional active such as salicylic acid, require a lower pH in order for the additional active to be fully efficacious. These compositions are usually formulated to have a pH of from about 2.5 to about 5, more preferably from about 2.7 to about 4.

Optional Components

The topical compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

Optional components include emollients, oil absorbents, antimicrobial agents, binders, buffering agents, denaturants, cosmetic astringents, external analgesics, film formers, humectants, opacifying agents, perfumes, pigments, skin soothing and healing agents, preservatives, propellants, skin penetration enhancers, solvents, suspending agents, emulsifiers, cleansing agents, thickening agents, solubilising agents, waxes, sunscreens, sunless tanning agents, antioxidants and/or radical scavengers, chelating agents, anti-acne agents, anti-inflammatory agents, desquamation agents/exfoliants, organic hydroxy acids, vitamins and natural extracts. Nonexclusive examples of such materials are described in *Harry's Cosmeticology*, 7th Ed., Harry & Wilkinson (Hill Publishers, London 1982); in *Pharmaceutical Dosage Forms—Disperse Systems;* Lieberman, Rieger & Banker, Vols. 1 (1988) & 2 (1989); Marcel Decker,. Inc.; in *The Chemistry and Manufacture of Cosmetics, 2nd. Ed.,* deNavarre (Van Nostrand 1962–1965); and in *The Handbook of Cosmetic Science and Technology,* 1st Ed. Knowlton & Pearce (Elsevier 1993) can also be used in the present invention.

A. Emollients

The topical compositions of the subject invention generally comprise from about 1% to about 50%, preferably from about 3% to about 15% of a dermatologically acceptable emollient. Emollients tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. Sagarin, *Cosmetics, Science and Technology*, 2nd Edition, Vol. 1, pp. 32–43 (1972), incorporated herein by reference, contains numerous examples of materials suitable as an emollient. Illustrative examples of emollients include:

i) Straight and branched chain hydrocarbons having from about 7 to about 40 carbon atoms, such as dodecane, squalane, cholesterol, hydrogenated polyisobutylene, isohexadecane and the $C_7$–$C_{40}$ isoparaffins, which are $C_7$–$C_{40}$ branched hydrocarbons.

ii) $C_1$–$C_{30}$ alcohol esters of $C_1$–$C_{30}$ carboxylic acids and of $C_2$–$C_{30}$ dicarboxylic acids, e.g. isononyl isononanoate, isopropyl myristate, myristyl propionate, isopropyl stearate, isopropyl isostearate, methyl isostearate, behenyl behenate, dioctyl maleate, diisopropyl adipate, and diisopropyl dilinoleate.

iii) mono-, di- and tri-glycerides of $C_1$–$C_{30}$ carboxylic acids and ethoxylated derivatives thereof, e.g., caprylic/capric triglyceride, PEG-6 caprylic/capric triglyceride.

iv) alkylene glycol esters of $C_1$–$C_{30}$ carboxylic acids, e.g. ethylene glycol mono- and di-esters, and propylene glycol mono- and di-esters of $C_1$–$C_{30}$ carboxylic acids e.g., ethylene glycol distearate.

v) $C_1$–$C_{30}$ mono- and poly-esters of sugars and related materials. These esters are derived from a sugar or polyol moiety and one or more carboxylic acid moieties. Depending on the constituent acid and sugar, these esters can be in either liquid or solid form at room temperature. Examples include: glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester in which the carboxylic acid ester moieties are palmitoleate and arachidate in a 1:2 molar ratio, and the octaester of sucrose wherein the esterifying carboxylic acid moieties are laurate, linoleate and behenate in a 1:3:4 molar ratio. Other materials include cottonseed oil or soybean oil fatty acid esters of sucrose. Other examples of such materials are described in WO 96/16636, incorporated by reference herein. A particularly preferred material is known by the INCI name sucrose polycottonseedate vi) Organopolysiloxane oils. The organopolysiloxane oil may be volatile, non-volatile, or a mixture of volatile and non-volatile silicones. The term "non-volatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Non-volatile polysiloxanes are preferred. Suitable silicones are disclosed in U.S. Pat. No. 5,069,897, issued Dec. 3, 1991, which is incorporated by reference herein in its entirety. Preferred for use herein are organopolysiloxanes selected from the group consisting of polyalkylsiloxanes, alkyl substituted dimethicones, dimethiconols, polyalkylaryl siloxanes, and mixtures thereof. More preferred for use herein are polyalkylsiloxanes and cyclomethicones. Preferred among the polyalkylsiloxanes are dimethicones.

vii) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, partially and fully hydrogenated oils from the foregoing sources, and mixtures thereof.

viii) animal fats and oils, e.g. cod liver oil, lanolin and derivatives thereof such as acetylated lanolin and isopropyl lanolate. Lanolin oil is preferred.

ix) Also useful are $C_4$–$C_{20}$ alkyl ethers of polypropylene glycols, $C_1$–$C_{20}$ carboxylic acid esters of polypropylene glycols, and di-$C_8$–$C_{30}$ alkyl ethers, examples of which include PPG-14 butyl ether, PPG-15 stearyl ether, dioctyl ether, dodecyl octyl ether, and mixtures thereof.

B. Humectants

A highly preferred optional component is a humectant, particularly of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), glycerine, ethoxylated glycerine and propoxylated glycerine.

Also useful herein are sodium 2-pyrrolidone-5-carboxylate, guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; panthenol; sodium pyroglutamate (NaPCA), water-soluble glyceryl poly(meth)acrylate lubricants (such as Hispagel®) and mixtures thereof.

The above listed compounds may be incorporated singly or in combination. Preferred humectants are selected from glycerine, glyceryl polyacrylate, urea, panthenol and mixtures thereof.

C. Emulsifiers/Surfactants

Compositions herein preferably contain an emulsifier and/or surfactant, generally to help disperse and suspend the discontinuous phase within the continuous phase. A surfactant may also be useful if the product is intended for skin cleansing. For convenience hereinafter emulsifiers will be referred to under the term 'surfactants', thus 'surfactant(s)' will be used to refer to surface active agents whether used as emulsifiers or for other surfactant purposes such as skin cleansing. Known or conventional surfactants can be used in the composition, provided that the selected agent is chemically and physically compatible with essential components of the composition, and provides the desired characteristics. Suitable surfactants include silicone materials, non-silicone materials, and mixtures thereof.

The compositions of the present invention preferably comprise from about 0.05% to about 15% of a surfactant or mixture of surfactants. The exact surfactant or surfactant mixture chosen will depend upon the pH of the composition and the other components present.

Preferred surfactants are nonionic. Among the nonionic surfactants that are useful herein are those that can be broadly defined as condensation products of long chain alcohols, e.g. $C_{8-30}$ alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are $C_{10-30}$ alkyl groups, X is —$OCH_2CH_2$ (i.e. derived from ethylene glycol or oxide) or —$OCH_2CHCH_3$— (derived from propylene glycol or oxide), and n is an integer from about 6 to about 100, examples of which include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants, which are described in more detail in WO 98/04241.

Preferred among the nonionic surfactants are those selected from the group consisting of steareth-2, steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, $C_1$–$C_{30}$ fatty acid esters of $C_1$–$C_{30}$ fatty alcohols, alkoxylated derivatives of $C_1$–$C_{30}$ fatty acid esters of $C_1$–$C_{30}$ fatty alcohols, alkoxylated ethers of C1–C30 fatty alcohols, polyglyceryl esters of $C_1$–$C_{30}$ fatty acids, $C_1$–$C_{30}$ esters of polyols, $C_1$–$C_{30}$ ethers of polyols, alkyl phosphates, polyoxyalkylene fatty ether phosphates, fatty acid amides, acyl lactylates, and mixtures thereof. Examples of these non-silicon-containing surfactants include: polysorbate 20, polyethylene glycol 5 soya sterol, steareth-20, ceteareth-20, PPG-2 methyl glucose ether distearate, ceteth-10, polysorbate 80, polysorbate 60, glyceryl stearate, sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another emulsifier useful herein are fatty acid ester blends based on a mixture of sorbitan or sorbitol fatty acid ester and sucrose fatty acid ester, the fatty acid in each instance being preferably $C_8$–$C_{24}$, more preferably $C_{10}$–$C_{20}$. The preferred fatty acid ester emulsifier is a blend of sorbitan or sorbitol $C_{16}$–$C_{20}$ fatty acid ester with sucrose $C_{10}$–$C_{16}$ fatty acid ester, especially sorbitan stearate and sucrose cocoate. This is commercially available from ICI under the trade name Arlatone 2121.

The hydrophilic surfactants useful herein can alternatively or additionally include any of a wide variety of cationic, anionic, zwitterionic, and amphoteric surfactants such as are known in the art. See, e.g., McCutcheon's, *Detergents and Emulsifiers,* North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

A wide variety of anionic surfactants are also useful herein. See, e.g., U.S. Pat. No. 3,929,678, to Laughlin et al., issued Dec. 30, 1975, which is incorporated herein by reference in its entirety. Exemplary anionic surfactants include the alkoyl isethionates (e.g., $C_{12}$–$C_{30}$), alkyl and alkyl ether sulfates and salts thereof, alkyl and alkyl ether phosphates and salts thereof, alkyl methyl taurates (e.g., $C_{12}$–$C_{30}$), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilising group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$–$C_{30}$), and alkanoyl sarcosinates.

Preferred emulsions of the present invention include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$–$C_{30}$ pendant side chains. Still other useful dimethicone copolyols include materials having various cationic, anionic, amphoteric, and zwitterionic pendant moieties.

D. Thickening Agent (Including Thickeners and Selling Agents)

The compositions of the present invention can also comprise, a thickening agent, preferably from about 0.1% to about 5%, more preferably from about 0.1% to about 3%, and most preferably from about 0.25% to about 2%, of a thickening agent.

Suitable thickening agents include cellulose and derivatives such as cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers the hydroxy groups of the cellulose polymer is hydroyxalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful thickeners include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof. Also useful are acrylic acid/ethyl acrylate copolymers and the carboxyvinyl polymers sold by the B.F. Goodrich Company under the trade mark of Carbopol resins. Suitable Carbopol resins are described in WO98/22085.

Preferred compositions of the present invention include a thickening agent selected from carboxylic acid polymers, crosslinked polyacrylates, polyacrylamides, xanthan gum and mixtures thereof, more preferably selected polyacrylamide polymers, xanthan gum and mixtures thereof. Preferred polyacrylamides are predispersed in a water-immiscible solvent such as mineral oil and the like, containing a surfactant (HLB from about 7 to about 10) which helps to facilitate water dispersibility of the polyacrylamide. Most preferred for use herein is the non-ionic polymer under the CTFA designation: polyacrylamide and isoparaffin and laureth-7, available under the trade name Sepigel 305 from Seppic Corporation.

E. Anti-Inflammatory Agents

A safe and effective amount of an anti-inflammatory agent may be added to the compositions of the subject invention, preferably from about 0.1% to about 5%, more preferably from about 0.1% to about 2%, of the composition. The anti-inflammatory agent enhances the skin appearance benefits of the present invention, e.g., such agents contribute to a more uniform and acceptable skin tone or colour. The exact amount of anti-inflammatory agent to be used in the compositions will depend on the particular anti-inflammatory agent utilised since such agents vary widely in potency.

Anti-inflammatory agents useful herein include steroids such as hydrocortisone; non-steroidal anti-inflammatory drugs (NSAIDS) such as ibuprofen; panthenol and ether and ester derivatives thereof e.g. panthenol ethyl ether, panthenyl triacetate; pantothenic acid and salt and ester derivatives thereof, especially calcium pantothenate; aloe vera, bisabolol, allantoin and compounds of the liquorice (the plant genus/species *Glycyrrhiza glabra*) family, including glycyrrhetic acid, glycyrrhizic acid, and derivatives thereof e.g. salts such as ammonium glycyrrhizinate and esters such as stearyl glycyrrhetinate. Particularly preferred herein are panthenol, pantothenic acid and their ether, ester or salt derivatives and mixtures thereof; suitable levels are from about 0.1 to about 5%, preferably from about 0.5 to about 3%. Panthenol is especially preferred.

F. Sunscreens and Sunblocks

Compositions of the subject invention can contain a sunscreen. Suitable sunscreens can be organic or inorganic. Especially preferred organic sunscreens include butylmethoxy-dibenzoylmethane, 2-ethylhexyl-p-methoxycinnamate, phenyl benzimidazole sulfonic acid, and octocrylene. Inorganic sunscreens include zinc oxide and titanium dioxide. Amounts of the sunscreen used are typically from about 1% to about 20%, more typically from about 2% to about 10%. Exact amounts will vary depending upon the sunscreen chosen and the desired Sun Protection Factor (SPF). An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

G. Anti-Oxidants/Radical Scavengers

Compositions of the subject invention can further include an anti-oxidant/radical scavenger. The anti-oxidant/radical scavenger is especially useful for providing protection against UV radiation which can cause increased scaling or texture changes in the stratum corneum and against other environmental agents which can cause skin damage. Suitable amounts are from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), β-carotene, tocopherol (vitamin E), tocopherol sorbate, tocopherol acetate, other esters of tocopherol, butylated hydroxy benzoic acids and their salts, gallic acid and its alkyl esters, especially propyl gallate, uric acid and its salts and alkyl esters, sorbic acid and its salts, amines (e.g., N,N-diethylhydroxylamine, amino-guanidine), sulfhydryl compounds (e.g., glutathione), dihydroxy fumaric acid and its salts, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol acetate, tocopherol sorbate and other esters of tocopherol, more preferably tocopherol acetate.

H. Chelators

The inclusion of a chelating agent is especially useful for providing protection against UV radiation which can contribute to excessive scaling or skin texture changes and against other environmental agents which can cause skin damage. A suitable amount is from about 0.01% to about 1%, more preferably from about 0.05% to about 0.5%, of the composition. Exemplary chelators that are useful herein are disclosed in U.S. Pat. No. 5,487,884, incorporated herein by reference. Preferred chelators useful in compositions of the subject invention are ethylenediamine tetraacetic acid (EDTA), furildioxime and derivatives thereof.

I. Desquamation Agents/Exfoliants

A safe and effective amount of a desquamation agent may be added to the compositions of the subject invention, more preferably from about 0.1% to about 10%, even more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including organic hydroxy acids such as salicylic acid, glycolic acid, lactic acid, 5-octanoyl salicylic acid, hydroxyoctanoic acid, hydroxycaprylic acid, and lanolin fatty acids. One desquamation system that is suitable for use herein comprises sulphydryl compounds and zwitterionic surfactants and is described in WO 96/01101, incorporated herein by reference. Another desquamation system that is suitable for use herein comprises salicylic acid and zwitterionic surfactants and is described in WO 95/13048, incorporated herein by reference. Salicylic acid is preferred.

J. Skin Lightening Agents

The compositions of the present invention can also comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art, including kojic acid, arbutin, ascorbic acid and derivatives thereof, e.g., magnesium ascorbyl phosphate. Further skin lightening agents suitable for use herein also include those described in WO 95/34280 and WO 95/23780; each incorporated herein by reference.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Skin Condition

The compositions of the present invention are useful for regulating mammalian skin condition, especially human skin, more especially that of the hands or other non-facial parts of the body, including regulating visible and/or tactile discontinuities in skin, e.g., visible and/or tactile discontinuities in skin texture, more especially discontinuities associated with skin ageing. Regulating skin condition involves topically applying to the skin a safe and effective amount of a composition of the present invention. The amount of the composition which is applied, the frequency of application and the period of use will vary widely depending upon the active levels of a given composition and the level of regulation desired, e.g., in light of the level of skin ageing present in the subject and the rate of further skin ageing.

A wide range of quantities of the compositions of the present invention can be employed to provide a skin appearance and/or feel benefit. Quantities of the present compositions which are typically applied per application are, in mg composition/$cm^2$ skin, from about 0.1 mg/$cm^2$ to about 10 mg/$cm^2$. A particularly useful application amount is about 2 mg/$cm^2$. Typically applications would be on the order of about once per day, however application rates can vary from about once per week up to about three times per day or more.

The compositions of this invention provide a visible improvement in skin condition essentially immediately following application of the composition to the skin. Such immediate improvement involves coverage or masking of skin imperfections such as textural discontinuities (including those associated with skin ageing,, such as enlarged pores), and/or providing a more even skin tone or colour.

The compositions of the invention also provide visible improvements in skin condition following chronic topical application of the composition. "Chronic topical application" and the like involves continued topical application of the composition over an extended period during the subject's lifetime, preferably for a period of at least about one week, more preferably for a period of at least about one month, even more preferably for at least about three months, even more preferably for at least about six months, and more preferably still for at least about one year. Chronic regulation of skin condition involves improvement of skin condition following multiple topical applications of the composition to the skin. Typically applications would be on the order of about once per day over such extended periods, however application rates can vary from about once per week up to about three times per day or more.

Regulating skin condition is preferably practised by applying a composition in the form of a skin lotion, cream, cosmetic, or the like which is intended to be left on the skin for an extended period for some aesthetic, prophylactic, therapeutic or other benefit (i.e., a "leave-on" composition). As used herein, "leave-on" compositions exclude rinse-off skin cleansing products. After applying the composition to the skin, the leave-on composition is preferably left on the skin for a period of at least about 15 minutes, more preferably at least about 30 minutes, even more preferably at least about 1 hour, most preferably for at least several hours, e.g., up to about 12 hours.

EXAMPLES

The following examples further describe and demonstrate embodiments within the scope of the present invention. The examples are given solely for the purpose of illustration and are not to be construed as limitations of the present invention. Where applicable, ingredients are given in CTFA name. All of the examples are oil-in-water emulsions prepared using conventional formulating techniques.

| Ingredient | Example 1 % w/w | Example 2 % w/w | Example 3 % w/w |
|---|---|---|---|
| Niacinamide | 2.5 | 4.0 | 3.0 |
| Retinyl propionate | | | 0.2 |
| Tospearl ® 145[1] | 6.0 | 9.0 | 3.0 |
| EA-209 ®[2] | 1.5 | | 1.0 |
| Polyacrylamide & isoparaffin & laureth-7 | 2.0 | 2.0 | 1.0 |
| Xanthan gum | | 0.6 | 0.3 |
| Titanium dioxide | | 0.5 | 0.3 |
| Glycerine | 7.0 | 5.0 | 3.0 |
| Urea | | | 2.0 |
| Panthenol | 1.0 | | |
| Salicylic acid | | 1.5 | |
| Allantoin | 0.2 | 0.1 | |
| Aloe vera gel | | | 0.05 |
| Tocopheryl acetate | | | 0.05 |
| Cetyl alcohol | 2.0 | 1.0 | 1.25 |
| Stearyl alcohol | 2.0 | 1.0 | 1.25 |
| Cyclomethicone & dimethiconol | 0.75 | 0.5 | 0.50 |
| Steareth-21 | 0.6 | 0.4 | 0.3 |
| Steareth-2 | 0.1 | 0.08 | 0.03 |
| Sorbitan stearate & sucrose cocoate | 1.5 | | |
| PPG-15 stearyl ether | 3.0 | 5.0 | 4.00 |
| Sucrose polycottonseedate | 2.0 | 3.0 | |
| Dimethicone (350 mm²s⁻¹) | 0.5 | | 0.50 |
| Disodium EDTA | 0.02 | 0.01 | 0.02 |
| Deionised water | to 100% | to 100% | to 100% |

| Ingredient | Example 4 % w/w | Example 5 % w/w | Example 6 % w/w |
|---|---|---|---|
| Niacinamide | 2.0 | 2.0 | 2.0 |
| Tospearl ® 145[1] | 6.0 | 12.0 | 3.0 |
| EA-209 ®[2] | 2.0 | | |
| Urea | 2.0 | 2.0 | 2.0 |
| Xanthan gum | 0.28 | 0.28 | 0.28 |
| Allantoin | | | 0.10 |
| Glyceryl monostearate & PEG-100 stearate | | 2.0 | |
| Sorbitan stearate & sucrose cocoate | | | 5.0 |
| Cetearyl alcohol | 1.0 | | 3.0 |
| Cetyl acetate & acetylated lanolin alcohol | 3.0 | 3.0 | 2.0 |
| Dimethicone & dimethiconol | 2.0 | 2.0 | 2.0 |
| Glycerine | 7.0 | 7.0 | 9.0 |
| Glyceryl stearate | 1.5 | | |
| DMDM Hydantoin & iodopropynyl-butylcarbamate | | | 0.1 |
| Lanolin oil | 3.0 | 3.0 | 2.0 |
| Arachidyl alcohol & behenyl alcohol & arachidylglucoside | | 3.0 | |
| Panthenol | | | 2.0 |
| PEG-30 glyceryl stearate | 2.4 | | |
| Phenoxyethanol | 0.4 | 0.4 | |
| Polyglyceryl-2-sesquiisostearate | 0.8 | | |
| Propylene glycol monostearate | 1.5 | | |
| Parabens | 0.4 | 0.4 | |
| Sucrose polycottonseedate | 2.0 | 1.0 | 1.0 |
| Polyacrylamide & isoparaffin & laureth-7 | 1.0 | 0.7 | 1.0 |
| Tetrasodium EDTA | 0.1 | 0.1 | 0.1 |
| Titanium dioxide | | | 0.15 |
| Deionised water | to 100% | to 100% | to 100% |

| Ingredient | Example 7 % w/w | Example 8 % w/w |
|---|---|---|
| Niacinamide | 2.0 | 3.5 |
| Nylon 12 | 1.0 | 2.0 |
| Polyacrylamide & isoparaffin & laureth-7 | 3.0 | 1.5 |
| Predispersed Titanium dioxide & glycerine & water & ammonium polyacrylate | 0.25 | 0.6 |
| Glycerine | 10.0 | 9.0 |
| Urea | | 1.0 |
| Panthenol | 1.0 | 1.0 |
| Allantoin | 0.2 | |
| Tocopheryl acetate | 0.75 | 0.5 |
| Cetyl alcohol | 0.7 | 1.4 |
| Stearyl alcohol | 0.5 | 1.6 |
| Cyclomethicone & dimethiconol | 2.0 | 1.0 |
| Isopropyl isostearate | 0.5 | 2.0 |
| Isohexadecane | 3.0 | 0.5 |
| PEG100 stearate | 0.1 | 0.1 |
| Sorbitan stearate & sucrose cocoate | 1.0 | 0.5 |
| Stearic acid | 0.1 | 0.2 |
| Sucrose polycottonseedate | 1.0 | 2.0 |
| Benzyl alcohol | 0.25 | 0.25 |
| Parabens | 0.4 | 0.5 |
| Sodium Hydroxide | 0.1 | 0.1 |
| Disodium EDTA | 0.1 | 0.1 |
| Deionised water | to 100% | to 100% |

[1]Polymethylsilsesquioxane, median particle size about 4.5 μm, supplied by Toshiba Silicone Co. Ltd.
[2]Ethylene/acrylic acid copolymer, median particle size about 10 μm, supplied by Kobo.

On application to a subject's hands, at the rate of 2mg/cm² skin, an essentially immediate visual improvement in skin appearance is provided e.g., reduced visibility of pores and a more even skin tone. Continuation of application, at the same rate once or twice daily for a period of 3–6 months improves skin surface texture, including diminishing fine lines and wrinkles, in addition to the essentially immediate improvements in appearance.

What is claimed is:

1. A topical composition comprising a) from 0.5% to 25% of a first particulate material having a refractive index of from 1.3 to 1.7, the particulate material being dispersed in the composition and having a median particle size of from 2 to 30 μm;

b) a safe and effective amount of an active effective for chronically regulating skin condition selected from Vitamin B3 compounds, retinoids, and mixtures thereof; and c) a topical carrier.

2. The composition of claim 1 wherein the active is selected from niacinamide, retinol esters, and mixtures thereof.

3. The composition of claim 1 wherein the active is niacinamide.

4. The composition of claim 1 which comprises from 0.1% to 15% of the active.

5. The composition of claim 1 wherein the particles of the first particulate material are solid.

6. The composition of claim 1 which comprises from 1% to 20%, especially from 2% to 12% of the first particulate material.

7. The composition of claim 1 wherein the first particulate material has a refractive index of from 1.35 to 1.6.

8. The composition of claim 1 wherein the first particulate material has a median particle size of from 2 to 15 μm.

9. The composition of claim 1 further comprising from 0.1 to 5% of a second particulate material having a refractive index of from 1.3 to 1.7, and a median particle size of from 8 to 30 μm, and wherein further the ratio of the median particle size of the first particulate to that of the second particulate is less than 0.75.

10. The composition of claim 1 which is an oil-in-water emulsion.

11. A cosmetic method of regulating skin condition comprising topically applying the composition of claim 1.

12. A method according to claim 11 wherein the composition is applied to non-facial parts of the body.

13. A method according to claim 12 wherein the composition is applied to the hands.

* * * * *